(12) United States Patent
Fonseca et al.

(10) Patent No.: US 7,662,579 B2
(45) Date of Patent: Feb. 16, 2010

(54) CYTOGENETICALLY DETERMINED PROGNOSIS OF MYELOMA

(75) Inventors: Rafael Fonseca, Rochester, MN (US); Philip R. Greipp, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 459 days.

(21) Appl. No.: 10/705,134

(22) Filed: Nov. 10, 2003

(65) Prior Publication Data

US 2004/0101898 A1 May 27, 2004

Related U.S. Application Data

(60) Provisional application No. 60/425,119, filed on Nov. 8, 2002.

(51) Int. Cl.
*G01N 33/574* (2006.01)
(52) U.S. Cl. .......................................... 435/7.23; 435/6
(58) Field of Classification Search ........................ None
See application file for complete search history.

(56) References Cited

OTHER PUBLICATIONS

Könisberg et al, J Clin Oncol, 2000, 18:804-812.*
Bergsagel et al, PNAS, 1996, 93:13931-13936.*
Ahmann et al, Cancer Genet Cytogenet, 1998, 101:7-11.*
Avet-Loiseau et al, Cancer Res, 1998, 58:5640-5645.*
Ackermann et al., "Absence of p53 deletions in bone marrow plasma cells of patients with monoclonal gammopathy of undedetermined significance," Br. J. Haematol., 103:1161-1163 (1998).
Avet-Loiseau et al., "P53 deletion is not a frequent event in multiple myeloma," Br. J. Haematol., 106:717-719 (1999).
Avet-Loiseau et al., "14q32 Translocations and Monosomy 13 Observed in Monoclonal Gammopathy of Undetermined Significance Delineate a Multistep Process for the Oncogenesis of Multiple Myeloma," Cancer Res., 59:4546-4550 (1999).
Avet-Loiseau et al., "High Incidence of Cryptic Translocations Involving the Ig Heavy Chain Gene in Multiple Myeloma, as Shown by Fluorescence in Situ Hybridization," Genes Chromosomes Cancer, 24:9-15 (1999).
Avet-Loiseau et al., "Chromosome 13 abnormalities in multiple myeloma are mostly monosomy 13," Br. J. Haematol., 111:1116-1117 (2000).
Chesi et al., "Dysregulation of Cyclin D1 by Translocation Int an IgH Gamma Switch Region in Two Multiple Myeloma Cell Lines," Blood, 88:674-681 (1996).
Chesi et al., "Frequent Dysregulation of the c-*maf*Proto-Oncogene at 16q23 by Translocation to an Ig Locus in Multiple Myeloma," Blood, 91:4457-4463 (1998).
Chesi et al., "The t(4;14) Translocation in Myeloma Dysregulates Both *FGFR3* and a Novel Gene, *MMSET*, Resulting in IGH/MMSET Hybrid Transcripts," Blood, 92:3025-3034 (1998).
Corradini et al., "Inactivation of Tumor Suppressor Genes, p53 and Rb1, in Plasma Cell Dyscrasias," Leukemia, 8:758-767 (1994).

Dewald et al., "The Clinical Significance of Cytogenetic Studies in 100 Patients With Multiple Myeloma, Plasma Cell Leukemia, or Amyloidosis," Blood, 66:380-390 (1985).
Drach et al., "Presence of a p53 Gene Deletion in Patients with Multiple Myeloma Predicts for Short Survival After Conventional-Dose Chemotherapy," Blood, 92:802-809 (1998).
Drach et al., "'Blood Doping' With Recombinant Erythropoietin (rhEPO) and Assessment of Functional Iron Deficiency in Healthy Volunteers," Br. J. Haematol., 108:883-886 (2000).
Facon et al., "Chromosome 13 abnormalities identified by FISH analysis and serum $\beta_2$-microglobulin produce a powerful myeloma staging system for patients receiving high-dose therapy," Blood, 97:1566-1571 (2001).
Finelli et al., "Detection of t(4;14)(p16.3;q32) Chromosomal Translocation in Multiple Myeloma by Double-Color Fluorescent in Situ Hybridization," Blood, 94:724-732 (1999).
Fonseca, et al., "Multiple myeloma and the translocation t(11;14)(q13;q32): a report on 13 cases," Br. J. Haematol., 101:296-301 (1998).
Fonseca et al., "The t(4;14)(p16.3;q32) is strongly associated with chromosome 13 abnormalities in both multiple myeloma and monoclonal gammopathy of undetermined significance," Blood, 98:1271-1272 (2001).
Fonseca et al., "Deletions of chromosome 13 in multiple myeloma identified by interphase FISH usually denote large deletions of the q arm or monosomy," Leukemia, 15:981-986 (2001).
Fonseca et al., "Genomic abnormalities in monoclonal gammopathy of undetermined significance," Blood, 100:1417-1424 (2002).
Fonseca et al., "Biological and Prognostic Significance of Interphase Fluorescence in Situ Hybridization Detection of Chromosome 13 Abnormalities (Δ13) in Multiple Myeloma: An Eastern Cooperative Oncology Group Study," Cancer Res., 62:715-720 (2002).
Fonseca et al., "Myeloma and the t(11;14)(q13;132); evidence for a biologically defined unique subset of patients," Blood, 99:3735-3741 (2002).
Hayman et al., "Translocations involving the immunoglobulin heavy-chain locus are possible early genetic events in patients with primary systemic amyloidosis," Blood, 98:2266-2268 (2001).
Janssen et al., "Concurrent activation of a novel putative transforming gene, myeov, and cyclin D1 in a subset of multiple myeloma cell lines with t(11;14)(q13;q32)," Blood, 95:2691-2698 (2000).
Moreau et al., "Recurrent 14q32 translocations determine the prognosis of multiple myeloma, especially in patients receiving intensive chemotherapy," Blood, 100:1579-1583 (2002).
"Multiple Myeloma: a Disease Overview," New Canaan, CT: Multiple Myeloma Research Foundation (2001).
Neri et al., "p53 Gene Mutations in Multiple Myeloma Are Associated With Advanced Forms of Malignancy," Blood, 81:128-135 (1993).
Perfetti et al., "Translocation t(4;14)(p16.3;q32) Is a Recurrent Genetic Lesion in Primary Amyloidosis," Am. J. Pathol., 158:1599-1603 (2001).

(Continued)

*Primary Examiner*—Misook Yu
*Assistant Examiner*—Mark Halvorson
(74) *Attorney, Agent, or Firm*—Fish & Richardson P.C.

(57) ABSTRACT

The invention provides methods and materials for determining a prognosis for myeloma and myeloma-disposed patients. The methods include the use of FISH techniques. The identification of the chromosomal abnormalities t(4;14)(p16;q32), t(14;16)(q32;q23), or 17p13 deletion (p53) in plasma cells from a patient indicates a poor prognosis.

10 Claims, 4 Drawing Sheets

OTHER PUBLICATIONS

Richelda et al., "A Novel Chromosomal Translocation t(4;14)(p16.3;q32) in Multiple Myeloma Involves the Fibroblast Growth-Factor Receptor 3 Gene," Blood, 90:4062-4070 (1997).

Schreiber et al., "Multiple myeloma with deletion of chromosome 13q is characterized by increased bone marrow neovascularization," Br. J. Haematol., 110:605-609 (2000).

Shaughnessy Jr., et al., "High incidence of chromosome 13 deletion in multiple myeloma detected by multiprobe interphase FISH," Blood, 96:1505-1511 (2000).

Shaughnessy Jr., et al., "Cyclin D3 at 6p21 is dysregulated by recurrent chromosomal translocations to immunoglobulin loci in multiple myeloma," Blood, 98:217-223 (2001).

Shou, et al., "Diverse karyotypic abnormalities of the c-myc locus associated with c-myc dysregulation and tumor progression in multiple myeloma," PNAS, 97:228-233 (2000).

Zojer et al., "Deletion of 13q14 remains an independent adverse prognostic variable in multiple myeloma despite its frequent detection by interphase fluorescence in situ hybridization," Blood, 95:1925-1930 (2000).

Avet-Loiseau et al., "High Incidence of Translocations t(11;14)(q13;q32) and t(4;14)(p16;q32) in Patients with Plasma Cell Malignancies," Cancer Research 58:5640-5645 (1998).

Chesi et al., "Frequent translocation t(4;14)(p16.3;q32.3) in multiple myeloma is associated with increased expression and activating mutations of fibroblast growth factor receptor 3," Nature Genetics 16:260-264 (1997).

Mazars et al., "Mutations of the p53 gene in human myeloma cell lines," Oncogene 7:1015-1018 (1992).

Preudhomme et al., "Rare occurrence of P53 gene mutations in multiple myeloma," British J. of Hematology 81:440-443 (1992).

Harrison et al. "Chromosomal Abnormalities in Systemic AL Amyloidosis" VIII Int'l Myeloma Workshop, Banff, Alberta, Canada, p. 18 (2001).

Avet-Loiseau et al., "A Comprehensive FISH Analysis Identifies Myeloma Patient Subgroups with Different Outcome," American Society of Hematology Annual Meeting (43rd; Dec. 2001; Florida, USA); abstract published on-line Nov. 16, 2001.

Fonseca et al., "A Molecular Classification of Multiple Myeloma (MM), Based on Cytogenetic Abnormalities Detected by Interphase FISH, is Powerful in Identifying Discrete Groups of Patients with Sissimilar Prognosis," American Society of Hematology Annual Meeting (43rd; Dec. 2001; Florida, USA); abstract published on-line Nov. 16, 2001.

Fonseca et al., "Clinical and biologic implications of recurrent genomic aberrations in myeloma," Blood 101:4569-4575, 2003.

* cited by examiner

CYTOGENETICALLY DETERMINED PROGNOSIS OF MYELOMA

RELATED APPLICATIONS

This application claims the benefit of U.S. Provisional Application No. 60/425,119, filed Nov. 8, 2002, which is incorporated herein by reference in its entirety.

GOVERNMENT SUPPORT

The work described herein was carried out, at least in part, using funds from the U.S. government under grant number R01 CA83724-01, awarded by the National Cancer Institute. The government may therefore have certain rights in the invention.

TECHNICAL FIELD

This invention relates to determining prognoses for myeloma, and more particularly to use of fluorescence in situ hybridization (FISH) to detect particular cytogenetic abnormalities, and correlation of such abnormalities with prognosis for myeloma.

BACKGROUND

There are over 14,000 new patients diagnosed with myeloma every year, and there is a need for better treatment and management strategies for this group of patients.

In most cases of multiple myeloma, reciprocal chromosomal translocations, mediated by errors in immunoglobulin heavy chain (IgH) switch recombination or somatic hypermutation are found to occur in plasma cells as they are generated in germinal centers. These translocations disregulate an oncogene that is repositioned in proximity to a strong IgH enhancer. The three most common chromosomal partners identified in these transformation events are chromosome 11 (at band q13 (i.e., 11q13); cyclin D1 locus), chromosome 4 (at band p16 (i.e., 4p16); FGFR3 and MMSET loci), and chromosome 16 (at band q23 (i.e., 16q23); c-maf locus). The translocation t(11;14)(q13;q32) is the most common IgH translocation in multiple myeloma.

SUMMARY

Methods and materials for determining a prognosis for a myeloma patient or a myeloma-disposed patient have been discovered and are provided herein. The methods and materials utilize fluorescence in situ hybridization (FISH) techniques to identify chromosomal abnormalities in a myeloma or myeloma-disposed patient.

A "myeloma-disposed patient" has an increased risk of developing a myeloma. A myeloma-disposed patients can be a patient diagnosed with Monoclonal Gammopathy of Undetermined Significance (MGUS), solitary plasmacytoma, or primary systemic amyloidosis (PSA).

In one embodiment, a method is provided for determining a prognosis for a myeloma patient or a myeloma-disposed patient, which includes (i) providing a sample of plasma cells from a patient, (ii) performing fluorescence in situ hybridization (FISH) analysis on the plasma cells, and (iii) classifying the patient as exhibiting a poor, intermediate or good prognosis based on the results of the FISH analysis. Discovery of a t(4;14)(p16;q32) (e.g., t(4;14)(p16.3;q32)) or t(14;16)(q32; q23) translocation, or a 17p13 deletion (p53) in a plasma cell from a patient indicates a poor prognosis. Discovery of a Δ13 chromosomal abnormality indicates an intermediate prognosis. Preferably a patient diagnosed as having an intermediate prognosis does not have a t(4;14)(p16;q32) or t(14;16)(q32; q23) translocation, or a 17p13 deletion. Discovery of other chromosomal abnormalities, including but not limited to a t(11;14)(q13;32) translocation, indicates a good prognosis. Preferably a patient diagnosed as having a good prognosis does not have a t(4;14)(p16;q32) or t(14;16)(q32;q23) translocation, or a 17p13 or Δ13 deletion.

A variety of FISH techniques are known in the art. FISH techniques that are particularly useful for identifying a chromosomal abnormality include, but are not limited to, interphase FISH and cIg-FISH.

The methods described herein can further include notifying a health care provider of the patient's prognosis. A "health care provider," can be any caregiver, such as a healthcare worker, including a doctor, nurse or other clinician; a guardian, such as a parent; another family member; or a teacher, minister or friend.

The methods described herein can also include recording a prognosis in print or in a computer readable format.

Also provided are kits that include nucleic acid probes specific for one or more of the chromosomal aberrations described. Exemplary nucleic acid probes can hybridize to a t(4;14)(p16;q32) (e.g., t(4;14)(p16.3;q32)), t(14;16)(q32; q23), or t(11;14)(q13;32) translocation, or a 17p13 or Δ13 deletion. The kits can also include informational materials, such as instructions for using the probes to perform a FISH analysis, such as on a plasma cell of a myeloma patient or myeloma-disposed patient. The kit can also include instructions for classifying the patient as exhibiting a poor, intermediate or good prognosis based on the results of the FISH analysis.

There are many advantages to the invention. For example, identifying subgroups of myeloma patients can permit the ability to focus the most appropriate treatments to each specific subgroup, thereby saving time and expense. The increased efficiency of treatment can also help ensure that a patient is getting the most appropriate treatment as earlier as possible, thereby increasing quality of life standards.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, useful methods and materials are described below. The materials, methods, and examples are illustrative only and not intended to be limiting. Other features and advantages of the invention will be apparent from the accompanying drawings and description, and from the claims. The contents of all references, pending patent applications and published patents, cited throughout this application are hereby expressly incorporated by reference. In case of conflict, the present specification, including definitions, will control.

DESCRIPTION

It has been found that specific subgroups of myeloma patients (e.g., multiple myeloma (MM) patients) identified by recurrent genetic aberrations, are at high risk of early death. The testing of newly diagnosed myeloma patients for these abnormalities is useful for the clinical management of these patients. Provided herein are methods for identifying genetic aberrations in humans having a myeloma and other diseases caused (at least partially) by abnormalities in plasma cell (PC) generation and division. Characterization of the genetic aberrations further leads to a prediction of survival time. Thus the type of genetic aberration identified leads to a prognosis of good, intermediate, or poor survivability. The median survival times of patients in these subgroups is 50.5, 42.3, and 24.7 months (p<0.001), respectively.

Multiple myeloma is a type of cancer formed by malignant plasma cells (PCs). Normal PCs are formed from B lymphocytes in response to an infection, and they produce antibodies that target and kill disease-causing agents, such as bacteria. PCs that grow out of control can produce a tumor, particularly in bone marrow, and multiple myeloma occurs when the tumors grow in multiple locations, within and without the bone marrow. Malignant PCs are identical and all produce the same kind of immunoglobulin protein called monoclonal (M) protein. A patient's myeloma can be referred to by the type of immunoglobulin or light chain (kappa- or lambda-type) produced by the cell. The most common myeloma types are IgG and IgA.

Methods for determining a prognosis for a human identified as having a myeloma are provided. These methods include examining a myeloma cell sample for the presence or absence of particular genetic rearrangements. A myeloma sample can be a sample of plasma cells, such as PCs isolated from bone marrow or blood. The method includes performing a fluorescence in situ hybridization (FISH) analysis, such as interphase FISH, including, for example, cIg-FISH, on cells of the myeloma cell sample, and based on the results of the analysis, classifying the patient as exhibiting a poor, intermediate, or good prognosis. Karyotype analysis can also be used to generate information on the chromosome integrity of a patient. The poor prognosis group includes MM patients identified as carrying t(4;14)(p16;q32) (including (t(4;14) (p16.3;q32)) or t(14;16)(q32;q23) translocations, or 17p13 deletions (including the p53 locus); the intermediate prognosis group is characterized by Δ13 chromosomal abnormalities (and preferably patients in this group do not carry any of the abnormalities of the poor prognosis group); and the good prognosis group includes all other chromosomal abnormalities. Patients in the good prognosis group preferably do not have any of the genetic aberrations of the poor and intermediate groups, and include patients who have a t(11;14)(q13; q32) translocation.

Figure 3:
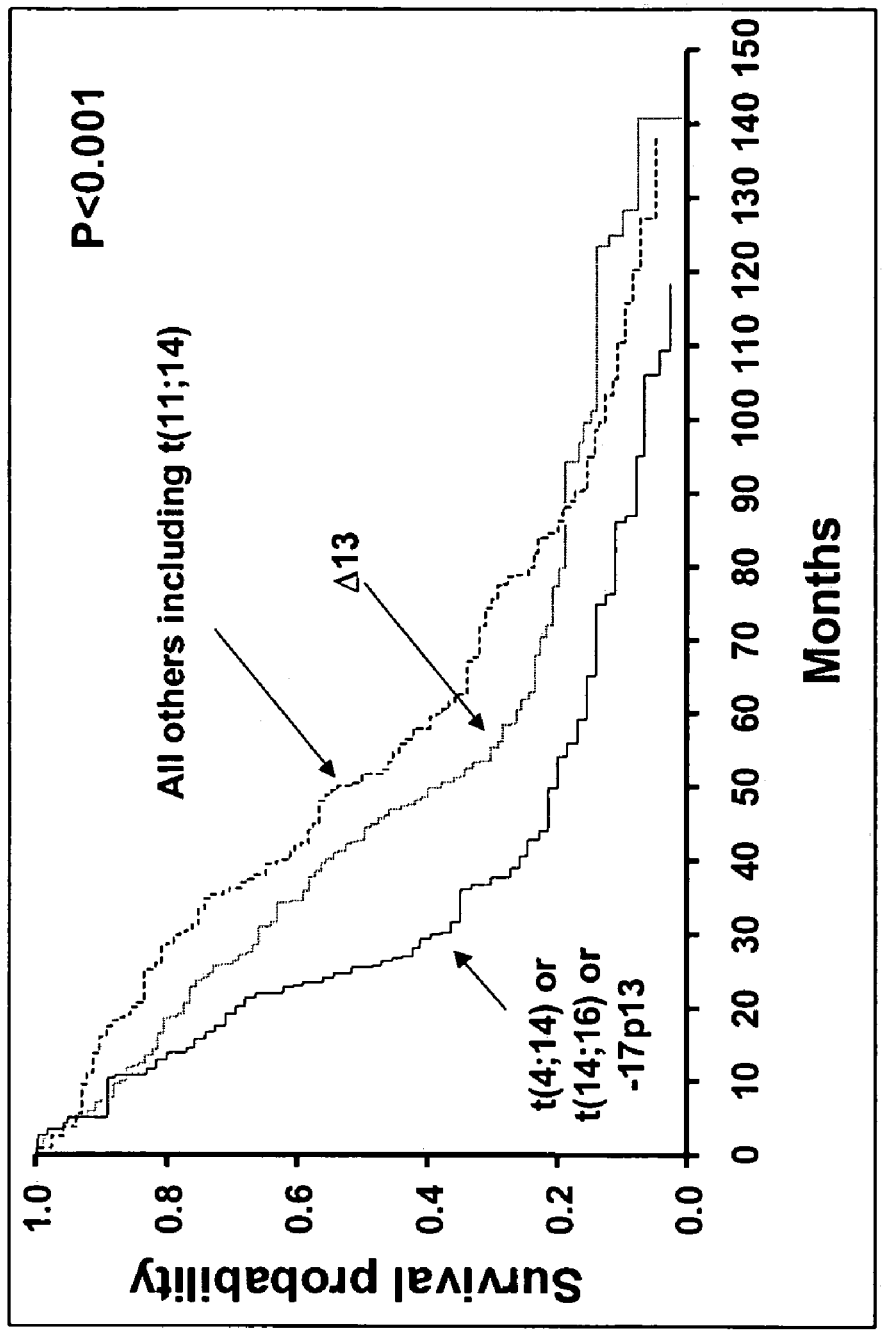
FIG. 3 is a graph illustrating the survival probability, over a course of 140 months, of a human having different chromosomal abnormalities.

In the studies reported below, a patient with a "poor" prognosis had a median survival time of about 24.7 months; a patient with an "intermediate" prognosis had a median survival time of about 42.3 months; and a patient with a "good" prognosis had a median survival time of about 50.5 months (see FIG. 3). These median survival times illustrate the distinctions between prognostic groups. The survival times could vary, however, with different populations of patients or as treatment regimens continue to develop.

The methods of the invention can potentially be used to assess the prognosis of humans diagnosed as having Monoclonal Gammopathy of Undetermined Significance (MGUS), solitary plasmacytoma, or primary systemic amyloidosis (PSA). A patient diagnosed as having any of these diseases is referred to herein as a "myeloma-disposed patient." In MGUS, abnormal plasma cells produce excess antibody protein. MGUS usually does not affect a person's health, but over time, many people with MGUS eventually develop multiple myeloma, lymphoma, or amyloidosis.

The abnormally dividing plasma cells in patients with solitary plasmacytomas typically result in the development of one tumor, rather than multiple tumors in different locations as in multiple myeloma. Such solitary tumors can occur in the bone marrow, lungs, or lining of the sinuses, throat or other organs. Many people with solitary plasmacytoma eventually develop multiple myeloma, especially if the plasmacytoma is in bone.

PSA is characterized by extracellular deposits of insoluble monoclonal immunoglobulin (Ig) light (L) chains or L-chain fragments (called amyloid) in various tissues, including smooth and striated muscles, connective tissues, blood vessel walls, and peripheral nerves. The amyloid of PSA is made by plasma cells in the bone marrow.

Figure 1:
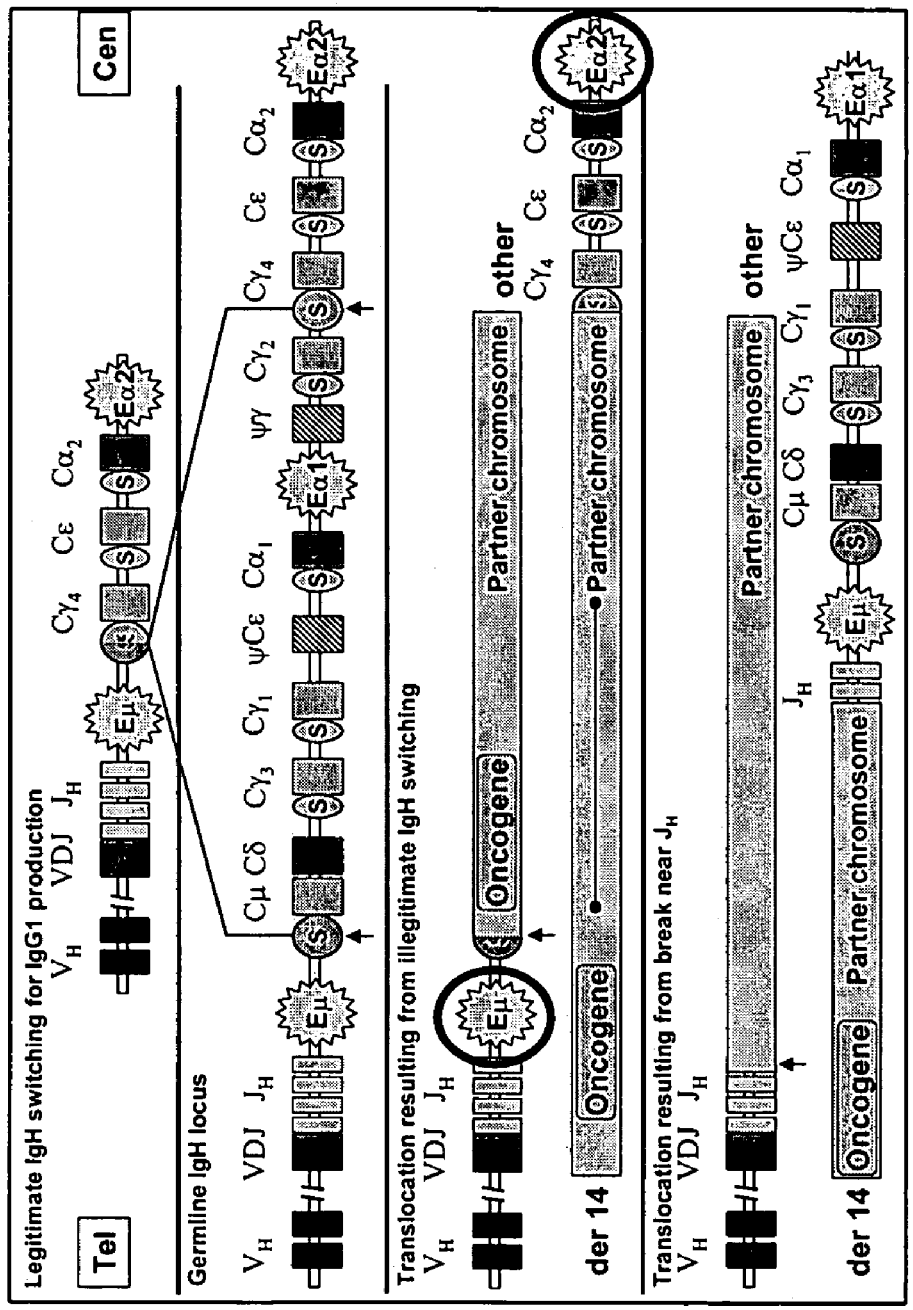
FIG. 1 is a cartoon of the immunoglobulin H (IgH) locus and IgH switching events. A "legitimate" switching event is necessary for IgG production; an "illegitimate" switching event common in myelomas results in a translocation that places two different enhancer elements (circled) adjacent to two oncogenes. Vertical arrows indicate chromosome breakpoints.
Figure 2:
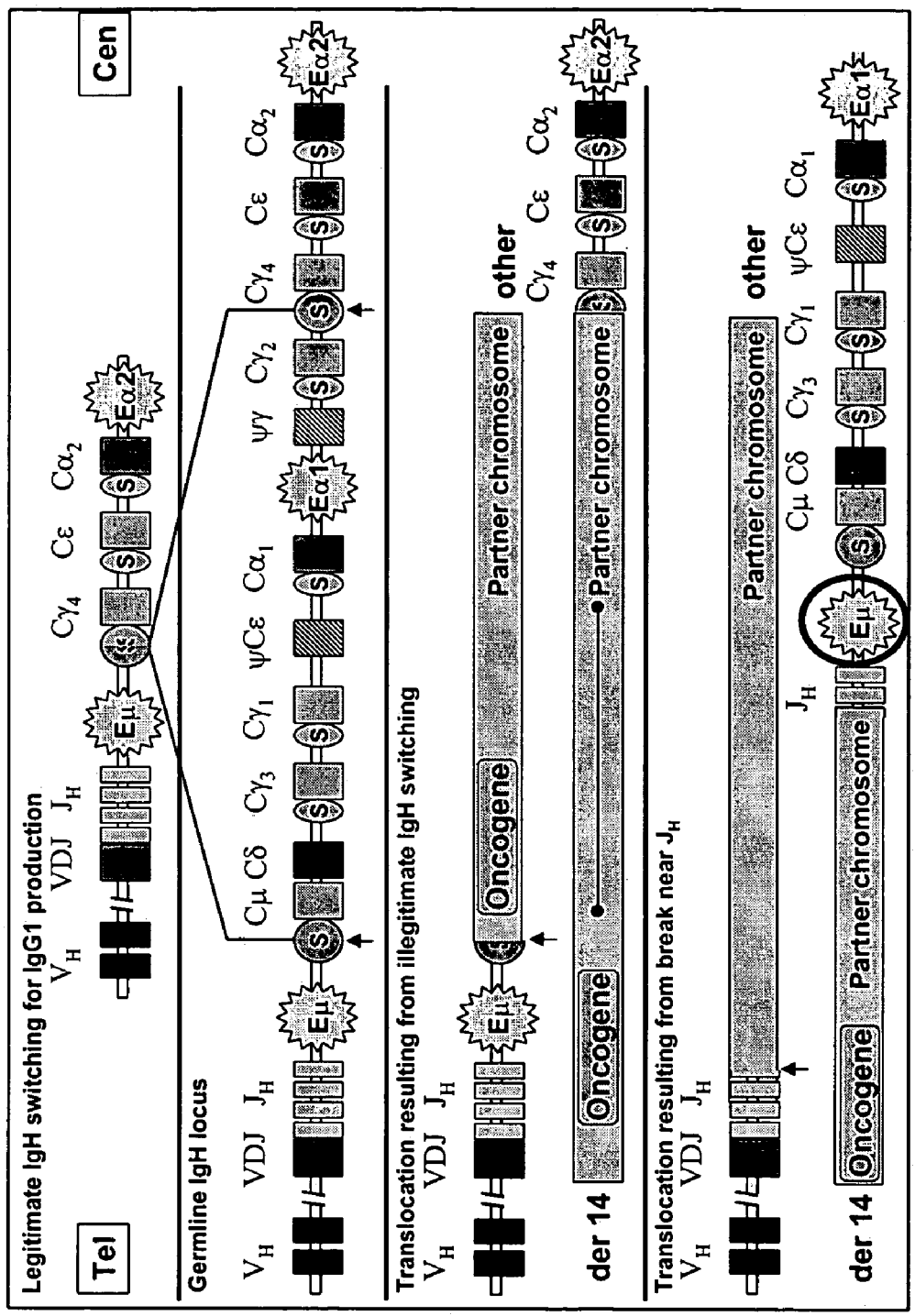
FIG. 2 is a cartoon of the IgH locus and IgH switching events. An illegitimate switching event places an enhancer element (circled) adjacent to an oncogene. Vertical arrows indicate chromosome breakpoints.

Genetic rearrangements The prognostic methods described herein can group individuals based on the presence of any number and variety of genetic rearrangements present in the disregulated PCs of the individuals. For example, a genetic rearrangement identified in a myeloma tissue sample can be an immunoglobulin heavy chain (IgH) switch translocation, which in some cases breaks the IgH locus into two parts. This can cause, for example, two enhancers to be juxtaposed to two or more potential oncogenes (see FIG. 1, for example). The misplaced enhancers can cause an increase in transcription (expression) of these genes, and can subsequently lead to pathogenesis. In another example, a genetic rearrangement in the cells of a myeloma tissue can be a rearrangement of an IgH joining ($J_H$) region (such as the $J_H$ region of the IgH locus on chromosome 14, band q32) or an IgH rearrangement that results in the disregulation of one oncogene on one chromosome (see FIG. 2, for example).

A human can be identified as having a t(4;14) translocation, such as a t(4;14)(p16;q32) translocation (e.g., a t(4;14) (p16.3;q32) translocation). A t(4;14)(p16;q32) translocation has breakpoints on chromosome 4 and 14, and at bands p16 and q32, respectively. The t(4;14)(p16.3;q32) is present in 10% to 20% of MM patients (Chesi et al., *Nat Genet.* 16:260-264, 1997; Chesi et al., *Blood* 92:3025-3034, 1998; Avet-Loiseau et al., *Cancer Res.* 58:5640-5645, 1998; Richelda et al., *Blood* 90:4062-4070, 1997; Fonseca et al., *Blood* 98:1271-1272, 2001), ~10% of patients with MGUS (Fonseca et al., *Blood* 100:1417-1424, 2002), and ~14% of patients with primary systemic amyloidosis (Perfetti et al., *Leukemia* 158:1599-1603, 2001). The t(4;14)(p16.3;q32) is almost always accompanied by a Δ13 chromosomal abnormality. This translocation typically results in the upregulation of FGFR3 and can also result in the hybrid transcript IgH/MMSET (Chesi et al., *Nat Genet.* 16:260-264, 1997; Chesi et al., *Blood* 92:3025-3034, 1998). Patients diagnosed as having a t(4;14) translocation, such as a t(4;14)(p16;q32), including a t(4;14)(p16.3, q32) translocation, have a poor prognosis.

A human can be identified as having a t(14;16) translocation, such as a t(14;16)(q32;q23) translocation. A t(14;16)(q32;q23) translocation type has been identified in about 25% of human MM cell lines. It is also cytogenetically cryptic, and has been detected in only about 5% of patients with MM (Chesi et al., *Blood* 91:4457-4463, 1998) and in a similar proportion of patients with MGUS (Fonseca et al., *Blood* 100:1417-1424, 2002). Breakpoints at 16q23 typically occur in the fragile site Fra16D region. This translocation results in upregulation of c-maf as a putative oncogene (Chesi et al., *Blood* 91:4457-4463, 1998). Patients diagnosed as having a t(14;16) translocation, such as t(14;16)(q32;q23), have a poor prognosis.

A human can be identified as having a chromosome 17p13 deletion, such as a 17p13.1 deletion, which results in mutations or deletions of the p53 locus. Chromosome 17p13.1 deletions have been detected in about 10% to 30% of patients with MM (Avet-Loiseau et al., *Br. J. Haematol.* 106:717-719, 1999; Drach et al., *Br. J. Haematol.* 108:886, 2000; Drach et al., *Blood* 92:802-809, 1998) and are infrequent in MGUS (Ackermann et al., *Br. J. Haematol.* 103:1161-1163, 1998). They have been associated with an adverse clinical outcome when detected in MM and Chronic Lymphocytic Leukemia (CLL) (Drach et al., *Blood* 92:802-809, 1998). Inactivating mutations of p53 have also been observed in MM more often in the advanced stages of the disease. They have been observed in ~5% of cases of early MM versus 20% to 40% of PC leukemia (Mazars et al., *Oncogene* 7:1015-1018, 1992; Corradini et al., *Leukemia* 8:758-767, 1994; Neri et al., *Blood* 81:128-135, 1993; Preudhomme et al., *Br. J. Haematol.* 81:440-443, 1992). Patients diagnosed as having a chromosome 17p13 deletion, such as a 17p13.1 deletion, have a poor prognosis.

A human can be identified as having a chromosome 13 abnormality. Chromosome 13 abnormalities (referred to herein as Δ13) are seen in 40% to 50% of patients with MM (Fonseca et al., *Leukemia* 15:981-986, 2001; Zojer et al., *Blood* 95:1925-1930, 2000; Facon et al., *Blood* 97:1566-1571, 2001). A Δ13 aberration can be a deletion of part or all of chromosome 13. For example, a patient having Δ13 can display monosomy for chromosome 13. Molecular mapping of Δ13 in MM has shown that when these abnormalities are detected by interphase FISH (in ~50% of patients), they indicate monosomy in 85% of patients with the abnormality, while the remaining 15% have an interstitial deletion (Fonseca et al., *Leukemia* 15:981-986, 2001; Avet-Loiseau et al., *Br. J. Haematol.* 111:1116-1117, 2000). Δ13 abnormalities are typically clonally selected in MM, so that when present, they are seen in the majority of clonal PCs (Fonseca et al., *Leukemia* 15:981-986, 2001; Avet-Loiseau et al., *Br. J. Haematol.* 111:1116-1117, 2000). Δ13 abnormalities are also typically associated with specific biologic features in MM, including a higher frequency of λ-type MM, slight female predominance, higher plasma cell labeling index (PCLI) (i.e., higher proliferative activity) and higher frequency of MM with a serum M component of less than 1 g/dl (Fonseca et al., *Cancer Res.* 62:715-720, 2002). The administration of interferon-α2 to MM patients with Δ13 can result in shorter overall survival (Fonseca et al., *Cancer Res.* 62:715-720, 2002). No specific gene has been identified as operative in Δ13 aberrations in MM. Patients diagnosed as having a chromosome 13 abnormality have an intermediate prognosis (see FIG. 3).

TABLE 1

Prevalence of Δ13 in the plasma cell disorders.

| Chromosome 13 abnormality | MGUS | MM |
|---|---|---|
| Mapping | Monosomy (?) | Monosomy (85%) |
| Proportion of abnormal PC, % | ~70 (30-100) | ~99 (80-100) |
| Prevalence, % | 30-50 | 50 |
| Clinical and prognostic significance | Unknown | Adverse |

A human can be identified as having a t(11;14)(q13;q32) translocation, which is the most common IgH translocation identified in MM (Dewald et al., *Blood* 66:380-390, 1985; Chesi et al., *Blood* 88:674-681, 1996). A t(11;14)(q13;q32) translocation results in cyclin D1 (Chesi et al., *Blood* 88:674-681, 1996) and myeov ("myeloma overexpressed gene") upregulation (Janssen et al., *Blood* 95:2691-2698, 2000). Translocations of t(11;14)(q13;q32) have been found in 25% of human MM cell lines (Chesi et al., *Blood* 88:674-681, 1996). This type of translocation has also been detected in MGUS (Avet-Loiseau et al., *Cancer Res.* 59:4546-4550, 1999; Fonseca et al., *Blood* 100:1417-1424, 2002) and primary systemic amyloidosis (PSA) (Hayman et al., *Blood* 98:2266-2268, 2001; Harrison et al., "Chromosomal abnormalities in systemic amyloidosis," Proceedings of the VIII International Myeloma Workshop. Banff, Alberta, Canada; 2001:P18). Patients diagnosed as having a t(11;14) translocation (e.g., a t(11;14)(q13;q32) translocation) have a good prognosis, provided that they do not have any of the aberrations that characterize a poor or intermediate prognosis (see FIG. 3).

Fluorescent In Situ Hybridization (FISH) Techniques The methods to determine the prognosis of a patient having multiple myeloma, or any other plasma cell derived disorder described herein, can include any type of FISH procedure, including interphase FISH and cytoplasmic immunoglobulin FISH (cIg-FISH), or any combination of FISH techniques. Interphase FISH, for example, detects chromosomes in the interphase stage of cell division, when chromosomes are less compact, thereby increasing map resolution (such as for mapping breakpoints and other genetic abnormalities) to around 100 kb. FISH that is not performed during interphase is more likely to result in a DNA mapping resolution of about 2-5 Mb. Interphase FISH is typically performed when cells are retaining cytoplasm, which allows cytomorphologic criteria to select only those PCs to be scored.

The chromosomal abnormalities discussed herein can be detected by the method of cIg-FISH (also called TRI-color FISH or FICTION). cIg-FISH utilizes immunofluorescence detection of PCs, such as bone marrow plasma cells. For example, an antibody that recognizes the light-chain antibody of a PC in a patient (e.g., an anti-kappa or anti-lambda light chain antibody) is conjugated to a label (such as 7-amino-4-methylcourmarin-3-acitic acid (AMCA, Vector Laboratories, Burlingame, Calif.) that is distinguishable from the labels used to detect the chromosomal aberrations in any one experiment (Shaughnessy et al., *Blood* 96:1505-1511, 2000). The use of this third label highlights the PCs in a sample, which are the cells most likely to exhibit a chromosomal aberration. This technique limits the scoring to plasma cells that share the same light-chain as the monoclonal (M) protein (Fonseca et al., *Leukemia* 15:981-986, 2001).

To detect the chromosomal translocations discussed herein and further to determine a prognosis, at least two sets of probes can be used. For example, one probe type can target one breakpoint and a second probe can target a second breakpoint. For example, to detect a t(11, 14)(q13,q32) translocation, one FISH probe can target (e.g., hybridize to) 11q13, and a second probe can target 14q32. For one or both breakpoint regions, a collection of different probes can hybridize to each breakpoint region. Each set of probes for each different chromosomal breakpoint can have a different detectable label, such as a different fluorescent label. For example, all the cIg-FISH probes that target 11q13 can be conjugated to a red fluorophore label (such as Spectrum Red, Vysis, Inc., Downers Grove, Ill.), and all the cIg-FISH probes that target 14q32 can be conjugated to a green fluorophore label (such as Spectrum Red, Vysis, Inc., Downers Grove, Ill.). Detection of the red and green fluorescent labels on a single chromosome can indicate a translocation event.

In another FISH technique, referred to herein as a breakapart strategy, probes targeting different regions of the same chromosome (e.g., on different sides of a putative breakpoint) can be conjugated to different fluorescent labels, and the chromosomes can be assayed for a separation of fluorescent label. For example, a 14q32 translocation can be detected by a first set of FISH probes that target the variable region of the IgH locus at 14q32 and are labeled with one color fluorophore, and a second set of FISH probes that target the IgH constant region and are labeled with a second color fluorophore. Separation of the different colored labels can indicate a 14q32 translocation (Hayman et al., *Blood* 98:2266-2268).

A variety of fluorescent labels for use in FISH assays are known by those having skill in the art. Probes can be labeled directly with a fluorescent probe, such as with a Cy5- or Cy3-dUTP label, or indirectly, such as with a biotin-dUTP label or digoxygenin-dUTP label. In the case of an indirect label, an immunofluorescence detection technique can be applied following hybridization of the probe to the target chromosome. For example, an avidin-FITC secondary detection agent can bind a biotin label, and a rhodamine-antidigoxigenin secondary label can bind a digoxigenin labeled probe. Probes for use in FISH (e.g, interphase FISH and/or cIg-FISH) analysis are discussed in greater detail below.

General FISH Procedures Typically, cells are harvested from a biological sample using standard techniques. For example, cells can be harvested by centrifuging a biological sample such as blood, and resuspending the pelleted cells. Typically, the cells are resuspended in phosphate-buffered saline (PBS). After centrifuging the cell suspension to obtain a cell pellet, the cells can be fixed, for example, in acid alcohol solutions, acid acetone solutions, or aldehydes such as formaldehyde, paraformaldehyde, and glutaraldehyde. For example, a fixative containing methanol and glacial acetic acid in a 3:1 ratio, respectively, can be used as a fixative. A neutral buffered formalin solution also can be used, and includes approximately 1% to 10% of 37-40% formaldehyde in an aqueous solution of sodium phosphate. Slides containing the cells can be prepared by removing a majority of the fixative, leaving the concentrated cells suspended in only a portion of the solution.

The cell suspension is applied to slides such that the cells do not overlap on the slide. Cell density can be measured by a light or phase contrast microscope. For example, cells harvested from a 20 to 100 ml urine sample typically are resuspended in a final volume of about 100 to 200 μl of fixative. Three volumes of this suspension (usually 3, 10, and 30 μl), are then dropped into 6 mm wells of a slide. The cellularity (i.e., density of cells) in these wells is then assessed with a phase contrast microscope. If the well containing the greatest volume of cell suspension does not have sufficient numbers of cells, the cell suspension is concentrated and placed in another well.

Prior to in situ hybridization, chromosomal probes and chromosomal DNA contained within the cell each are denatured. Denaturation typically is performed by incubating in the presence of high pH, heat (e.g., temperatures from about 70° C. to about 95° C.), organic solvents such as formamide and tetraalkylammonium halides, or combinations thereof. For example, chromosomal DNA can be denatured by a combination of temperatures above 70° C. (e.g., about 73° C.) and a denaturation buffer containing 70% formamide and 2×SSC (0.3M sodium chloride and 0.03 M sodium citrate). Denaturation conditions typically are established such that cell morphology is preserved. Chromosomal probes can be denatured by heat. For example, probes can be heated to about 73° C. for about five minutes.

After removal of denaturing chemicals or conditions, probes are annealed to the chromosomal DNA under hybridizing conditions. "Hybridizing conditions" are conditions that facilitate annealing between a probe and target chromosomal DNA. Hybridization conditions vary, depending on the concentrations, base compositions, complexities, and lengths of the probes, as well as salt concentrations, temperatures, and length of incubation. The higher the concentration of probe, the higher the probability of forming a hybrid. For example, in situ hybridizations are typically performed in hybridization buffer containing 1-2×SSC, 50% formamide and blocking DNA to suppress non-specific hybridization. In general, hybridization conditions, as described above, include temperatures of about 25° C. to about 55° C., and incubation lengths of about 0.5 hours to about 96 hours. More particularly, hybridization can be performed at about 32° C. to about 40° C. for about 2 to about 16 hours.

Non-specific binding of chromosomal probes to DNA outside of the target region can be removed by a series of washes. Temperature and concentration of salt in each wash depend on the desired stringency. For example, for high stringency conditions, washes can be carried out at about 65° C. to about 80° C., using 0.2× to about 2×SSC, and about 0.1% to about 1% of a non-ionic detergent such as Nonidet P-40 (NP40). Stringency can be lowered by decreasing the temperature of the washes or by increasing the concentration of salt in the washes.

Chromosomal probes typically are chosen for maximal sensitivity and specificity. The probes generally range from about 50 to about $1 \times 10^5$ nucleotides in length. Longer probes typically comprise smaller fragments of about 100 to about 500 nucleotides in length. Probes that hybridize with centromeric DNA and locus-specific DNA are available commercially, for example, from Vysis, Inc. (Downers Grove, Ill.), Molecular Probes, Inc. (Eugene, Oreg.), or from Cytocell (Oxfordshire, UK). Alternatively, probes can be made non-commercially from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via the polymerase chain reaction (PCR). See, for example, Nath and Johnson, *Biotechnic Histochem.* 73:6-22, 1998, Wheeless et al., *Cytometry* 17:319-326, 1994; and U.S. Pat. No. 5,491,224.

Chromosomal probes typically are directly labeled with a fluorophore, an organic molecule that fluoresces after absorbing light of lower wavelength/higher energy. The fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, U.S. Pat. No. 5,491,224.

Fluorophores of different colors are chosen such that each chromosomal probe in the set can be distinctly visualized. For example, a combination of the following fluorophores may be used: 7-amino-4-methylcoumarin-3-acetic acid (AMCA), Texas Red™ (Molecular Probes, Inc., Eugene, Oreg.), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4,4-difluoro-5,7-dimethyl-4-bora-3a,4a diaza-3-indacenepropionic acid, eosin-5-isothiocyanate, erythrosin-5-isothiocyanate, and Cascade™ blue acetylazide (Molecular Probes, Inc., Eugene, Oreg.). Probes are viewed with a fluorescence microscope and an appropriate filter for each fluorophore, or by using dual or triple band-pass filter sets to observe multiple fluorophores. See, for example, U.S. Pat. No. 5,776,688. Alternatively, techniques such as flow cytometry can be used to examine the hybridization pattern of the chromosomal probes.

Probes also can be indirectly labeled with biotin or digoxygenin, or labeled with radioactive isotopes such as $^{32}P$ and $^{3}H$, although secondary detection molecules or further processing then is required to visualize the probes. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Kits Kits for performing a genotype analysis are provided. A kit can include, for example, materials for identifying any of the genetic aberrations discussed herein. For example, a kit can include nucleic acid probes that hybridize specifically to any of the t(4;14)(p16;q32), t(14;16)(q32;q23), t(11;14)(q13;32), and t(4;14)(p16.3;q32) translocations; and the Δ13 and 17p13 deletions. A kit can further include reagents for using the nucleic acid probes to detect the genetic aberration, such as by a FISH technique. A kit can also include informational material. The informational material can include, for example, instructions for using the probes to perform a FISH analysis directed to detecting a chromosomal aberration in a plasma cell of a myeloma patient or myeloma-disposed patient, and instructions for classifying the patient as exhibiting a poor, intermediate or good prognosis based on the results of said FISH analysis.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about methods of detecting a genetic aberration and the interpretation of results. Of course, the informational material can also be provided in any combination of formats.

The composition of the kits (e.g., nucleic acid probes and reagents for performing a FISH analysis) can include other ingredients, such as a solvent or buffer, a stabilizer, and a preservative. Alternatively, the other ingredients can be included in the kit, but in different compositions or containers than the nucleic acid probes and/or reagents. In such embodiments, the kit can include instructions for admixing probes and the other ingredients.

The contents of the kit can be provided in any form, e.g., liquid, dried or lyophilized form. It is preferred that the nucleic acid probes and any detection reagents are substantially pure and/or sterile. When the nucleic acid probes are provided in a liquid solution, the liquid solution preferably is an aqueous solution, with a sterile aqueous solution being preferred. When the probes, for example, are provided as a dried form, reconstitution generally is by the addition of a suitable solvent. The solvent, e.g., sterile water or buffer, can optionally be provided in the kit.

The kit can include one or more containers for the composition containing the nucleic acid probes. In some embodiments, the kit contains separate containers, dividers or compartments for probes and reagents, and informational material. For example, the nucleic acid probes and reagents can be contained in a bottle, vial, or syringe, and the informational material can be contained in a plastic sleeve or packet. In other embodiments, the separate elements of the kit are contained within a single, undivided container. For example, a composition is contained in a bottle, vial or syringe that has attached thereto the informational material in the form of a label. In some embodiments, the kit includes a plurality (e.g., a pack) of individual containers, each containing one or more unit forms of a nucleic acid probe (e.g., one container for each individual use or assay). For example, a kit can include a plurality of ampules, vials, foil packets, or blister packs, each containing a single unit. The containers of the kits can be air tight and/or waterproof. The containers can be labeled for a particular use, such as for detecting a chromosomal aberration in a myeloid patient or a myeloid-disposed patient, for the purpose of providing a prognosis of the patient.

The kit optionally includes a device suitable for obtaining a biological sample, such as a plasma cell sample or tumor sample, from a patient, e.g., a scapula, syringe, or swab (e.g., a cotton swab or wooden swab), or any such tissue- or cell-collection device, for the purpose of performing a genotype analysis.

The invention is further illustrated by the following examples, which should not be construed as further limiting.

EXAMPLES

Example 1

Multiple Myeloma (MM) and the t(11;14)(q13;q32) Represent a Uniquely Defined Biological Subset of Patients Multiple myelomas were examined in more than 350 patients. Sixteen percent of the test group was found to carry the t(11;14)(p13;q32) translocation, and a striking association between the t(11;14)(q13;q32) and hypodiploid or pseudodiploid MM (by DNA content analysis) was also observed. This is in great contrast to what is observed in other MM samples where >65% are hyperdiploid. Patients with MM and the t(11;14)(q13;q32) translocation had a higher frequency of small monoclonal proteins, lymphoplasmacytic morphology and a lower prevalence of plasmacytomas. Contrary to previous beliefs, t(11;14)(q13;q32), MM patients appeared to have a better clinical outcome and response to treatment (Fonseca et al., *Br. J. Haematol.* 101:296-301, 1998). No relation was found between t(11;14)(q13;q32) and Δ13 abnormalities. This study provided the first assessment of the clinical/biologic significance of t(11;14)(q13;q32) in MM (Fonseca et al., *Br. J. Haematol.* 101:296-301, 1998).

Example 2

Chromosome 13 Abnormalities Represent a Unique Subgroup in Multiple Myeloma Patients The prognostic significance of Δ13 abnormalities, as detected by cIg-FISH, was examined in MM patients. Associations between Δ13 abnormalities and the oligo-secretory variant MM and λ light-chain were observed. An association between Δ13 and increased angiogenesis has been reported (Schreiber et al., *Br J Haematol.* 110:605-609, 2000), but was not observed in the present study. Although a correlation was observed between Δ13 and PCLI, there was a significant overlap between groups of patients (those with and without Δ13). In addition, patients with Δ13 had a worse outcome when treated with interferon-$\alpha_2$ than MM patients without Δ13 (Fonseca et al., *Cancer Res.* 62:715-720, 2002).

The deletion 13q14 is a type of Δ13 abnormality. A 13q14 deletion, detected by interphase FISH, was found to usually indicate a large deletion or monosomy. A group of 351 patients were studied, and it was found that when Δ13 abnormalities were present, they were usually seen in the majority of the clonal PCs. Two independent observers performed the scoring, and demonstrated a high level of concordance in the percentage of abnormal PCs observed ($r^2$=0.99). The median percentage of abnormal PCs was 97%. Telomeric "walking" experiments were performed in patients with and without 13q14 probe deletions to show that in the majority of cases patients had simultaneous loss of a sub-telomeric probe, likely indicating that in these patients (85%) 13q14 deletions represented monosomy (Fonseca et al., *Leukemia* 15:981-986, 2001).

Figure 4:
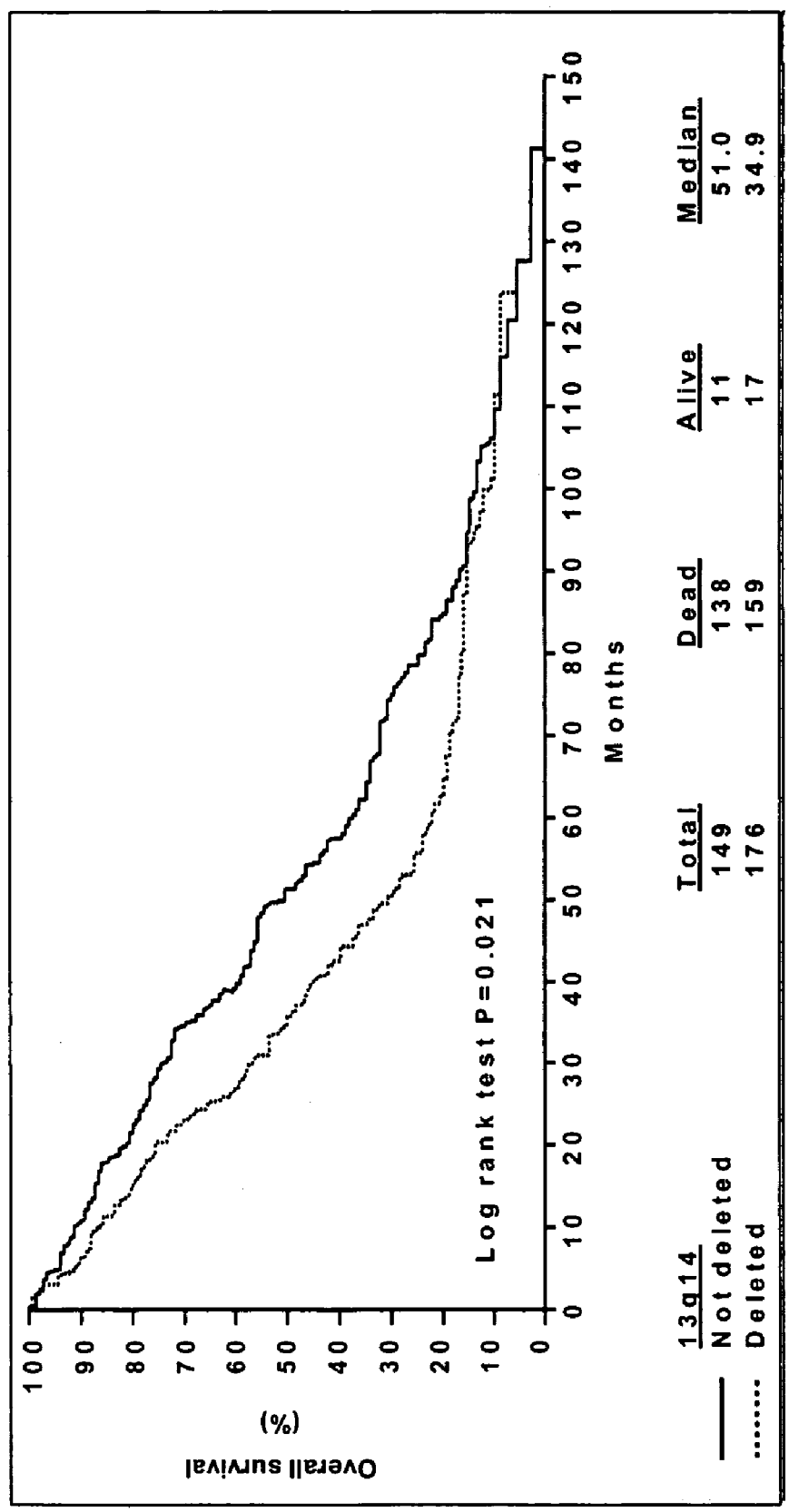
FIG. 4 is a graph illustrating a comparison of the survival rates, over a course of 140 months, between a group of individuals carrying a chromosome 13q14 deletion and a group of individuals carrying a chromosome 13 deletion (Δ13) that is not 13q14.

A group of 325 individuals identified as having Δ13 abnormalities was divided into two subgroups: one subgroup carried a 13q14 deletion, while the other subgroup did not carry a 13q14 deletion. Individuals carrying a 13q14 deletion were found to have a median shorter survival time, and therefore a worse prognosis, than individuals not carrying a 13q14 deletion (FIG. 4).

A model for the prognostic importance of all chromosomal abnormalities in multiple myeloma was developed. According to the model, patients are stratified into three distinct categories: (i) a poor prognosis group, carrying a t(4;14)(p16;q32) (including (t(4;14)(p16.3;q32)), t(14;16)(q32;q23), or 17p13 deletion (p53); (ii) an intermediate prognosis, characterized Δ13 abnormalities; and (iii) a good prognosis group, which includes all other chromosomal abnormalities. The median survival time of these groups is 24.7, 42.3, and 50.5 months, respectively (p<0.001) (FIG. 3).

OTHER EMBODIMENTS

A number of embodiments of the invention have been described. Nevertheless, it will be understood that various modifications can be made without departing from the spirit and scope of the invention. Accordingly, other embodiments are within the scope of the following claims.

What is claimed is:

1. A method for determining a prognosis for a myeloma patient or a myeloma-disposed patient, comprising:
   (i) performing fluorescence in situ hybridization (FISH) analysis on a sample of plasma cells from said patient to test for the presence or absence of a t(4;14)(p16;q32) translocation; and
   (ii) prognosing said patient based on the presence or absence of said t(4;14)(p16;q32) translocation, wherein said patient is determined to exhibit a poor prognosis if said plasma cells display said t(4;14)(p16;q32) translocation.

2. The method of claim 1, wherein said patient is determined to exhibit an intermediate prognosis if said plasma cells display a Δ13 chromosomal abnormality and do not display t(4;14)(p16;q32) translocation, and also do not display a t(14;16)(q32;q23) translocation, or a 17p13 deletion.

3. The method of claim 1, wherein said patient is determined to exhibit a good prognosis if said plasma cells do not display said t(4;14)(p16;q32) translocation, and also do not display a t(14;16)(q32;q23) translocation, a 17p13 deletion, or a Δ13 chromosomal abnormality.

4. The method of claim 1, wherein said t(4;14)(p16;q32) translocation is t(4;14)(p16.3;q32).

5. The method of claim 1, wherein said FISH analysis is interphase FISH.

6. The method of claim 1, wherein said FISH analysis is cytoplasmic immunoglobulin FISH (cIg-FISH) analysis.

7. The method of claim 1, further comprising notifying a health care provider of said prognosis.

8. The method of claim 1, further comprising recording said determination in print or in a computer readable format.

9. The method of claim 2, wherein said t(4;14)(p16;q32) translocation is t(4;14)(p16.3;q32).

10. The method of claim 3, wherein said t(4;14)(p16;q32) translocation is t(4;14)(p16.3;q32).

* * * * *

UNITED STATES PATENT AND TRADEMARK OFFICE
CERTIFICATE OF CORRECTION

PATENT NO. : 7,662,579 B2  Page 1 of 1
APPLICATION NO. : 10/705134
DATED : February 16, 2010
INVENTOR(S) : Rafael Fonseca It is certified that error appears in the above-identified patent and that said Letters Patent is hereby corrected as shown below:

Column 12, line 33 (Claim 2), after "display" please insert --said--;

Column 12, line 47 (Claim 7), please delete "prognosis" and insert --determination-- therefor.

Signed and Sealed this

Fifteenth Day of June, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,662,579 B2 | Page 1 of 1 |
| APPLICATION NO. | : 10/705134 | |
| DATED | : February 16, 2010 | |
| INVENTOR(S) | : Fonseca et al. | |

It is certified that error appears in the above-identified patent and that said Letters Patent is hereby corrected as shown below:

On the Title Page - Delete "459 days"

Item (*) Notice should read: Subject to any disclaimer, the term of this patent is extended or adjusted under 35 U.S.C. 154(b) by 814 days Signed and Sealed this Thirty-first Day of August, 2010

David J. Kappos
*Director of the United States Patent and Trademark Office*